(12) United States Patent
Howard

(10) Patent No.: US 6,368,313 B1
(45) Date of Patent: Apr. 9, 2002

(54) DOG DIAPER SYSTEM

(76) Inventor: Sandra K. Howard, 8112 Somerset Dr., Largo, FL (US) 33773

( * ) Notice: Subject to any disclaimer, the term of this patent is extended or adjusted under 35 U.S.C. 154(b) by 0 days.

(21) Appl. No.: 09/615,123

(22) Filed: Jul. 13, 2000

(51) Int. Cl.[7] .......................... A61F 13/15; A01K 13/00
(52) U.S. Cl. ........................ 604/385.09; 604/385.09; 604/393; 119/850
(58) Field of Search .................. 604/385.01, 385.09, 604/385.13–385.15, 386, 389, 392, 396; 119/850

(56) References Cited

U.S. PATENT DOCUMENTS

| | | | | |
|---|---|---|---|---|
| 4,813,949 A | * | 3/1989 | O'Rourke | 604/391 |
| 4,996,949 A | * | 3/1991 | Wunderman et al. | 119/143 |
| 5,005,525 A | * | 4/1991 | Stanton | 119/95 |
| 5,555,847 A | * | 9/1996 | Kelly | 119/850 |
| 5,662,640 A | * | 9/1997 | Daniels | 604/392 |

\* cited by examiner

Primary Examiner—John G. Weiss
Assistant Examiner—Jamisue Webb

(57) ABSTRACT

A dog diaper system. Pants are adapted to be worn over the hindquarters of a dog. The pants have a lower panel with a front end of an enlarged size, a back end of a reduced size and with side edges between the front end and back end. The pants also have an upper panel with a front end of an enlarged size and a back end of a reduced size with side edges between the front end and back end. Coupling components join the side edges of the upper panel and the lower panel. Enlarged leg holes extend through the pants and are located essentially equally between the front panel and the rear panel adjacent to the rear end. A small aperture is formed in the panels at the bottom end for the passage of a dog's tail. A strap couples the front end of the pants to the neck of the dog. A pad is coupled to the pants on the interior surface of the lower panel.

10 Claims, 4 Drawing Sheets

DOG DIAPER SYSTEM

BACKGROUND OF THE INVENTION

1. Field of the Invention

The present invention relates to a dog diaper system and more particularly pertains to precluding in-house damage caused by dog urination while maximizing the comfort to the dog.

2. Description of the Prior Art

The use of diaper systems of known designs and configurations is known in the prior art. More specifically, diaper systems of known designs and configurations previously devised and utilized for the purpose of minimizing in-house damage caused by dog urination through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,290,386 to Eiriksson discloses a dog sanitary device of a type including a harness and a removable receptacle. U.S. Pat. No. 4,444,152 to Berardo discloses a device for collection of animal wastes. U.S. Pat. No. 4,510,887 to Lincoln et al. discloses an animal fecal collection system. U.S. Pat. No. 4,577,591 to Wesseldine discloses an incontinence and protective device for animals. U.S. Pat. No. 5,005,525 to Stanton discloses an animal marking and urination control device. Lastly, U.S. Pat. No. 5,934,226 to Moore et al. discloses a bird diaper.

While these devices fulfill their respective, particular objectives and requirements, the aforementioned patents do not describe a dog diaper system that allows precluding in-house damage caused by dog urination while maximizing the comfort to the dog.

In this respect, the dog diaper system according to the present invention substantially departs from the conventional concepts and designs of the prior art, and in doing so provides an apparatus primarily developed for the purpose of precluding in-house damage caused by dog urination while maximizing the comfort to the dog.

Therefore, it can be appreciated that there exists a continuing need for a new and improved dog diaper system which can be used for precluding in-house damage caused by dog urination while maximizing the comfort to the dog. In this regard, the present invention substantially fulfills this need.

SUMMARY OF THE INVENTION

In view of the foregoing disadvantages inherent in the known types of diaper systems of known designs and configurations now present in the prior art, the present invention provides an improved dog diaper system. As such, the general purpose of the present invention, which will be described subsequently in greater detail, is to provide a new and improved dog diaper system and method which has all the advantages of the prior art and none of the disadvantages.

To attain this, the present invention essentially comprises a dog diaper system for precluding in-house damage caused by dog urination while maximizing the comfort to the dog. First provided are pants adapted to be worn over the hindquarters of a dog. The pants have a lower panel with a front end of an enlarged size and a back end of a reduced size. The lower panel also has side edges between the front end and the back end. The pants also have an upper panel with a front end of an enlarged size and a back end of a reduced size. The upper panel also has side edges between the front end and the back end. Stitching couples the side edges of the upper panel and the lower panel. Enlarged leg holes located essentially equally between the upper panel and the lower panel adjacent to the rear end extend through the pants. A dog's legs may pass through the leg holes. A small aperture is formed in the panels between the leg holes at the bottom end. A dog's tail may pass through the small aperture. The small aperture is of sufficient size to allow the dog to have a bowel movement without soiling the pants. The front end of the upper and lower panels is formed with a hollow hem. An elastic waistband is positioned within the hollow hem. The waistband has free ends extending exterior of the hem adjacent the midpoint of the upper panel. Inelastic tie strings are provided at the ends of the elastic waistband to accommodate dogs of various midsection sizes. A generally rectangular bib has stitching coupling the front end of the lower panel with the bib and extending forwardly from the bib. The entire pants and bib are formed of a fabric, natural of synthetic, or blends thereof, as for example cotton or spandex or interlock knit or blends thereof. The entire pants and bib have an interior surface positionable adjacent to the dog wearing the pants. The entire pants and bib have an exterior surface exposed. The entire exterior surface of the pants is adapted to have decorative indicia thereon. An elastic first strap is provided. The elastic first strap has free ends stitched to the front end of the bib. An elastic second strap is also provided. A rigid attachment loop in proximity to, but spaced forwardly of, the front end of the bib couples the first and second straps. An adjustment buckle provided on the second strap allows for varying lengths for a proper fitting to the neck of dogs of varying sizes. A pad has an interior surface formed of an absorbent material interiorly in contact with the dog. The pad also has an exterior surface formed of a moisture impervious plastic material. The exterior surface is greater in size than the absorbent material and is positioned in contact with the pants. The exterior surface extends rearwardly from adjacent to the front end of the bib to a location adjacent to the small hole. The pad has arcuate cutouts generally concentric with and in the region adjacent to the large leg holes. Lastly, an adhesive strip is provided. The adhesive strip couples the exterior surface of the pad with the interior surface of the lower panel from adjacent to the forward edge of the pad to adjacent to the rearward edge of the pad.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved dog diaper system which has all of the advantages of the prior art diaper systems of known designs and configurations and none of the disadvantages.

It is another object of the present invention to provide a new and improved dog diaper system which may be easily and efficiently manufactured and marketed.

It is further object of the present invention to provide a new and improved dog diaper system which is of durable and reliable constructions.

An even further object of the present invention is to provide a new and improved dog diaper system which is susceptible of a low cost of manufacture with regard to both materials and labor, and which accordingly is then susceptible of low prices of sale to the consuming public, thereby making such dog diaper system economically available to the buying public.

Even still another object of the present invention is to provide a dog diaper system for precluding in-house damage caused by dog urination while maximizing the comfort to the dog.

Lastly, it is an object of the present invention to provide a new and improved dog diaper system. In the system, pants are adapted to be worn over the hindquarters of a dog. The pants have a lower panel with a front end of an enlarged size, a back end of a reduced size and with side edges between the front end and back end. The pants also have an upper panel with a front end of an enlarged size and a back end of a reduced size with side edges between the front end and back end. Coupling components join the side edges of the upper panel and the side edges of the lower panel. Enlarged leg holes extend through the pants and are located essentially equally between the front panel and the rear panel adjacent to the rear end. A small aperture is formed in the panels at the bottom end for the passage of a dog's tail. A strap couples the front end of the pants to the neck of the dog. A pad is coupled to the pants on the interior surface of the lower panel.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
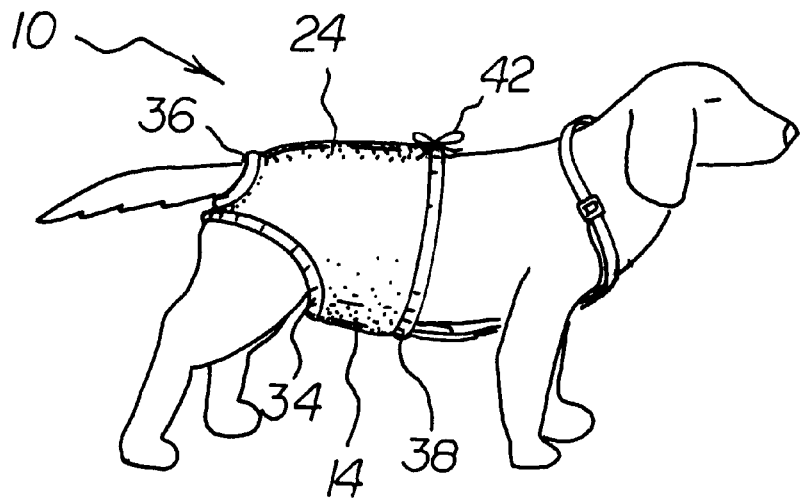
FIG. 1 is side elevational view of the dog diaper system constructed in accordance with the principles of the present invention.
Figure 2:
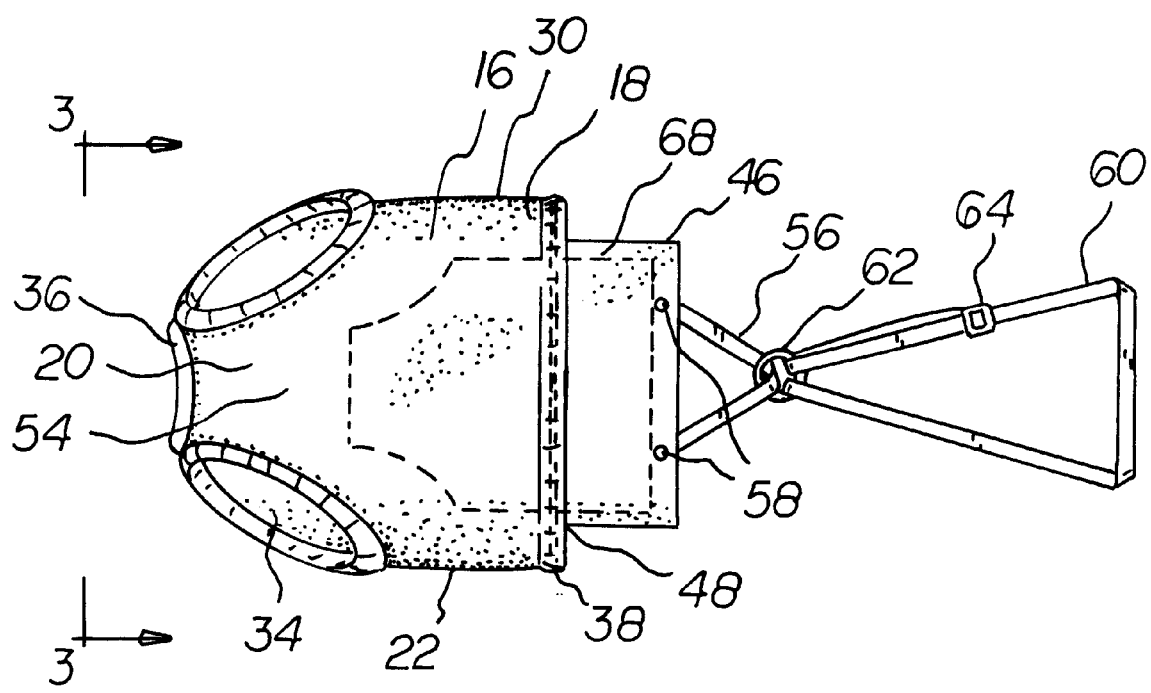
FIG. 2 is a bottom view of the system shown in FIG. 1.
Figure 3:
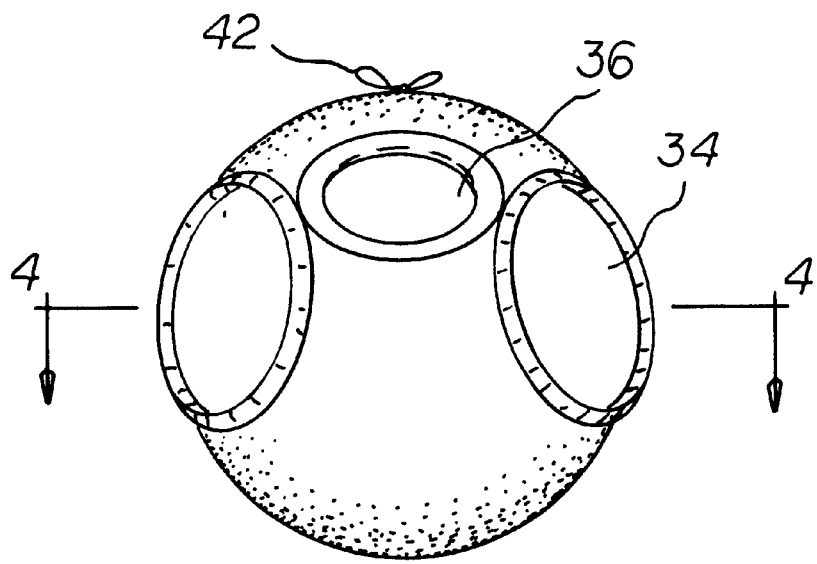
FIG. 3 is an end view taken along line 3—3 of FIG. 2.
Figure 4:
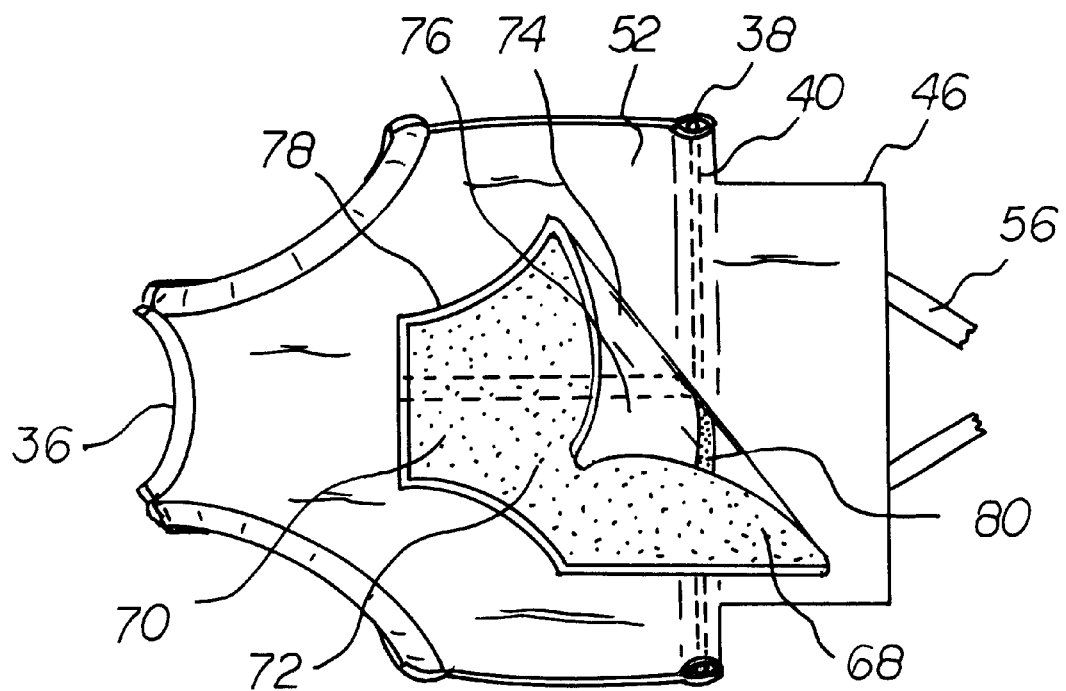
FIG. 4 is a cross sectional view of the system taken along line 4—4 of FIG. 3.

With reference now to the drawings, and in particular to FIG. 1 thereof, the preferred embodiment of the new and improved dog diaper system embodying the principles and concepts of the present invention and generally designated by the reference numeral 10 will be described.

The present invention, the dog diaper system 10 is comprised of a plurality of components. Such components in their broadest context include pants, a strap, and a pad. Such components are individually configured and correlated with respect to each other so as to attain the desired objective.

First provided as part of the system are pants 14. The pants are adapted to be worn over the hindquarters of a dog. The pants have a lower panel 16 with a front end 18 of an enlarged size and a back end 20 of a reduced size. The lower panel also has side edges 22 between the front end and the back end. The pants also have an upper panel 24 with a front end 26 of an enlarged size and a back end 28 of a reduced size. The upper panel also has side edges 30 between the front end and the back end. Stitching 32 couples the side edges of the upper panel and the side edges of the lower panel. Enlarged leg holes 34 located essentially equally between the upper panel and the lower panel adjacent to the rear end extend through the pants. In use, a dog's legs may pass through the leg holes. A small aperture 36 is formed in the panels between the leg holes at the bottom end. In use, a dog's tail may pass through the small aperture. The small aperture is of sufficient size to allow the dog to have a bowel movement without soiling the pants. The front end of the upper and lower panels is formed with a hollow hem 38. An elastic waistband 40 is positioned within the hollow hem. The waistband has free ends extending exterior of the hem adjacent the midpoint of the upper panel. Inelastic tie strings 42 are provided at the ends of the elastic waistband to accommodate dogs of various midsection sizes.

A generally rectangular bib 46 is next provided. Stitching 48 couples the front end of the lower panel with the bib. The bib extends forwardly from the front end of the lower panel.

The entire pants and bib are formed of a fabric, natural of synthetic, or blends thereof, as for example cotton or spandex or interlock knit or blends thereof. The entire pants and bid have an interior surface 52 positionable adjacent to the dog wearing the pants. The entire pants and bib have an exterior surface 54 exposed and adapted to have decorative indicia thereon.

An elastic first strap 56 is next provided. The first strap has free ends 58 stitched to the front end of the bib. An elastic second strap 60 is also provided. A rigid attachment loop 62 is provided. The rigid attachment loop is in proximity to, but spaced forwardly of, the front end of the bib. The loop couples the first and second straps. An adjustment buckle 64 is provided on the second strap. The adjustment buckle allows for varying lengths for a proper fitting to the neck of dogs of varying sizes.

A pad 68 is next provided. The pad has an interior surface 70 formed of an absorbent material 72 interiorly in contact with the dog. The pad also has an exterior surface 74 formed of a moisture impervious plastic material 76. The exterior surface is greater in size than the absorbent material and is positioned in contact with the pants. The exterior surface extends rearwardly from adjacent to the front end of the bib to a location adjacent to the small hole. The pad has arcuate cutouts 78 generally concentric with and in the region adjacent to the large leg holes.

Lastly, an adhesive strip 80 is provided. The adhesive strip couples the exterior surface of the pad with the interior surface of the lower panel from adjacent to the forward edge of the pad to adjacent to the rearward edge of the pad.

Figure 5:
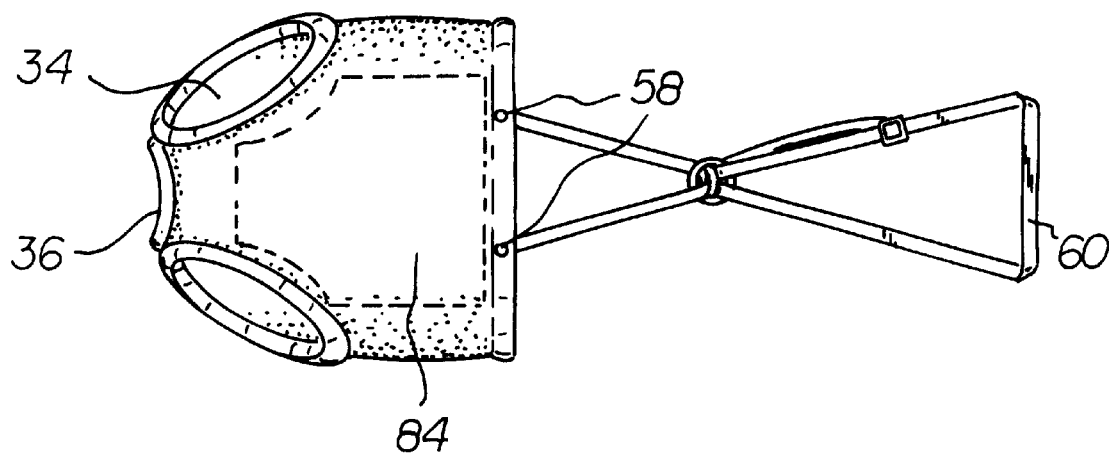
FIG. 5 is a bottom view of an alternate embodiment of the invention designed for use with female dogs.
Figure 6:
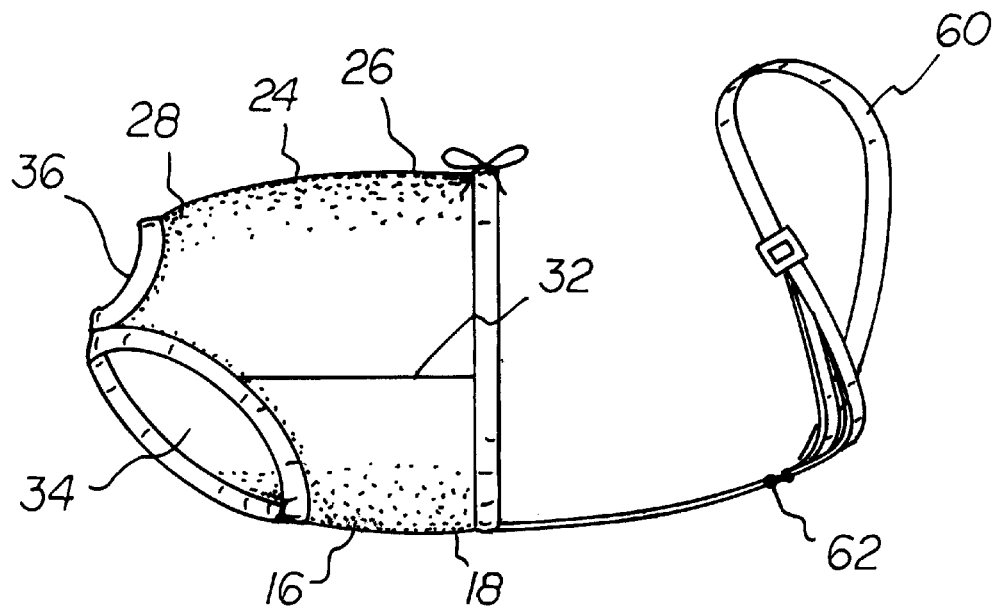
FIG. 6 is a side elevational view of the embodiment shown in FIG. 5.

In an alternate embodiment of the invention, as shown in FIG. 5, the pad 84 is fabricated of cloth which may be washed for reuse.

Figure 7:
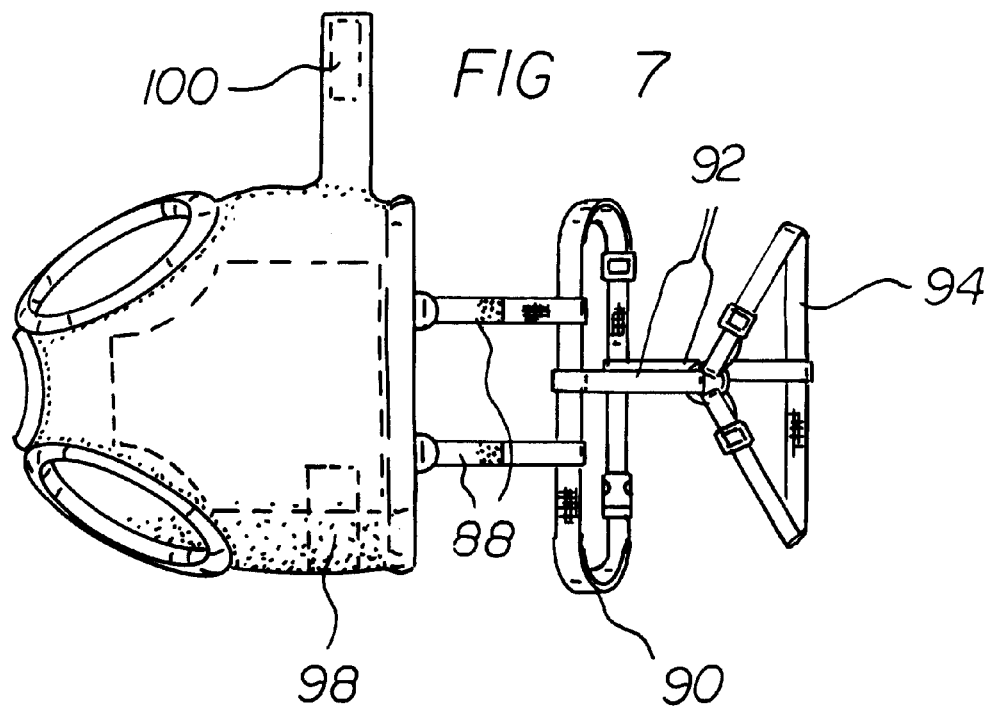
FIG. 7 is a bottom elevational view of a further alternate embodiment made for larger female dogs.
Figure 8:
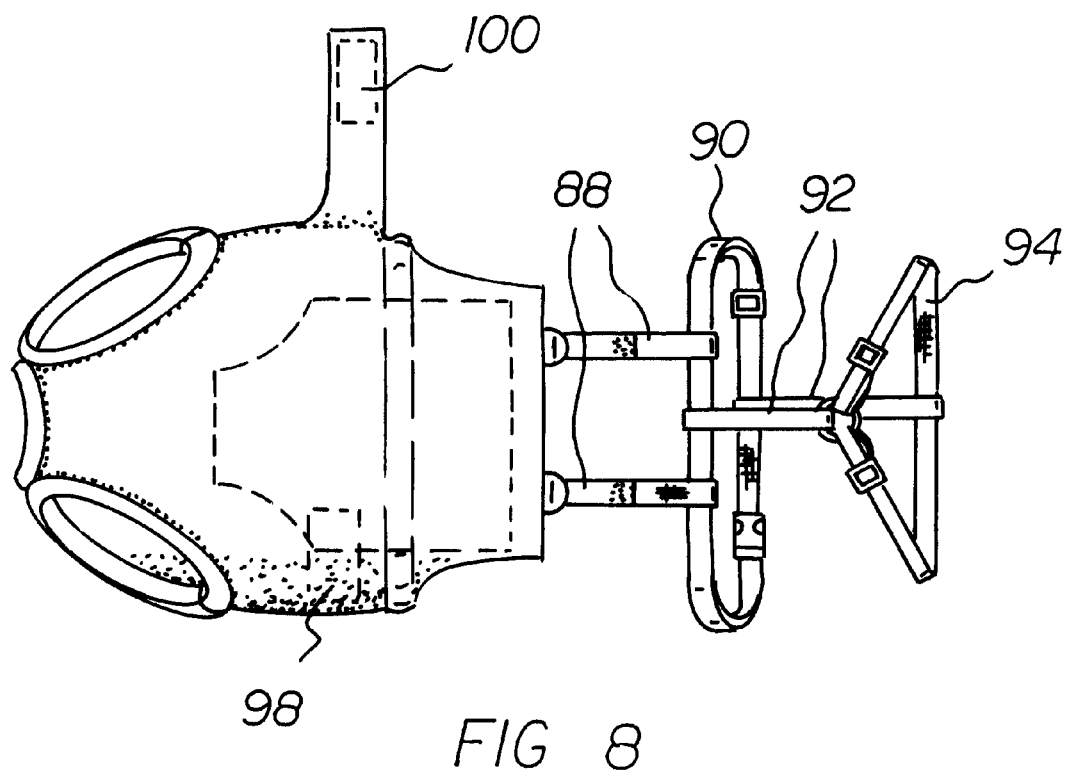
FIG. 8 is a bottom elevational view similar to FIG. 7 but designed for use with larger male dogs.

As shown in FIGS. 7 and 8, an alternate strap assembly for larger dogs includes two primary straps 88 extending forwardly from the front end of the pants, an enlarged circumferential large strap 90 positionable around the chest of a dog, two secondary straps 92 extending forwardly from the circumferential strap and a circumferential small strap 94 positionable around the neck of a dog.

As shown in FIGS. 7 and 8, an alternate embodiment includes pile type fasteners 98 on one of the panels and tabs with coacting pile type fasteners 100 on the other panel for releasable couplings to accommodate larger dogs.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dog diaper system for precluding in-house damage caused by a dog urination while maximizing the comfort to a dog comprising, in combination:

pants adapted to be worn over the hindquarters of a dog, the pants having a lower panel with a front end of an enlarged size and a back end of a reduced size and with side edges there between, the pants also having an upper panel with a front end of an enlarged size and a back end of a reduced size and with side edges there between, the side edges of the upper panel and the lower panel coupled together with the use of stitching, enlarged leg holes extending through the pants and located essentially equally between the upper panel and the lower panel adjacent to the back end for the passage of a dog's legs there between, a small aperture located where the upper and lower panels are connected at the back end of the panels between the leg holes for the passage of a dog's tail there through, the front ends of the upper and lower panels being formed with a hollow hem with an elastic waistband positioned therein, the waistband having ends extending exterior of the hem with inelastic tie strings at the ends of the elastic waistband to accommodate dogs of various midsection sizes;

a generally rectangular bib attached to the lower panel using stitching with the bib extending forwardly therefrom;

the entire pants and bib being formed of a fabric, natural or synthetic, or blends thereof, the entire pants and bib having an interior surface that is capable of being positioned adjacent to the dog wearing the pants and an exterior surface;

an elastic first strap having ends stitched to the bib and an elastic second strap that is capable of being positioned around the neck of the dog and a rigid attachment loop in proximity to, but spaced forwardly of, the bib and coupling the first and second straps and an adjustment buckle on the second strap for allowing a proper fitting to the neck of dogs of varying lengths;

a pad having an interior surface formed of an absorbent material in contact with the dog and having an exterior surface formed of a moisture impervious plastic material, greater in size than the absorbent material, positioned in contact with the pants extending from the bib to a location adjacent to the small aperture, the pad having arcuate cutouts in the region adjacent to the large leg holes and generally concentric therewith; and an adhesive strip coupling the exterior surface of the pad with the interior surface of the lower panel from adjacent to the forward edge of the pad to adjacent to the rearward edge of the pad.

2. A dog diaper system comprising pants adapted to be worn over the hindquarters of a dog, the pants having a lower panel with a front end of an enlarged size and a back end of a reduced size and with side edges there between, the pants also having an upper panel with a front end of an enlarged size and a back end of a reduced size and with side edges there between, coupling components joining the side edges of the upper panel to the side edges of the lower panel, enlarged leg holes extending through the pants and located essentially equally between the front panel and the rear panel adjacent to the rear end for the passage of a dog's legs there between, the panels having a small aperture formed therein between the leg holes at the bottom end for the passage of a dog's tail there through;

a strap assembly with an elastic first strap coupled to the front end of the pants and with an elastic second strap positionable around the neck of a dog with a rigid attachment loop coupling the first and second straps; and a pad coupled to the pants on the interior surface of the lower panel.

3. The system as set forth in claim 2 and further including a bib extending forwardly of the front end of the lower panel with the first strap coupled to the front end of the bib and the pad coupled to the interior surface of the bid and lower panel for male dogs.

4. The system as set forth in claim 2 wherein the first strap is coupled to the front end of the lower panel for female dogs.

5. The system as set forth in claim 2 wherein the pad has an interior surface formed of an absorbent material positionable in contact with a dog and having an exterior surface formed of a moisture impervious plastic material greater in size than the absorbent material positioned in contact with the pants extending rearwardly from adjacent to the front end of the bib rearwardly to a location adjacent to the small hole, the pad having arcuate cutouts in the region adjacent to the large leg holes and generally concentric therewith.

6. The system as set forth in claim 2 wherein the pad is fabricated of cloth which may be washed for reuse.

7. The system as set forth in claim 2 wherein the strap is an assembly with an elastic first strap coupled to the front end of the pants and with an elastic second strap positionable around the neck of a dog with a rigid attachment loop coupling the first and second straps.

8. The system as set forth in claim 2 wherein the coupling components include stitches for dogs of smaller sizes.

9. The system as set forth in claim 2 wherein the coupling components include pile type fasteners on one of the panels and tabs with coacting pile type fasteners on the other panel for releasable coupling to accommodate larger dogs.

10. A dog diaper system comprising pants adapted to be worn over the hindquarters of a dog, the pants having a lower panel with a front end of an enlarged size and a back end of a reduced size and with side edges there between, the pants also having an upper panel with a front end of an enlarged size and a back end of a reduced size and with side edges there between, coupling components joining the side edges of the upper panel to the side edges of the lower panel, enlarged leg holes extending through the pants and located essentially equally between the front panel and the rear panel adjacent to the rear end of the passage of a dog's legs there between, the panels having a small aperture formed therein between the leg holes at the bottom end of the passage of a dog's tail there through; and a strap assembly with two primary straps extending forwardly from the front end of the pants, an enlarged circumferential large strap positionable around the chest of a dog, two secondary straps extending forwardly from the circumferential strap and a circumferential small strap positionable around the neck of a dog.

* * * * *